United States Patent [19]

Brode et al.

[11] Patent Number: 5,595,980
[45] Date of Patent: Jan. 21, 1997

[54] CONTRACEPTIVE COMPOSITIONS

[75] Inventors: George L. Brode, Bridgewater, N.J.; Gustavo F. Doncel, Norfolk, Va.; Henry L. Gabelnick, N. Bethesda, Md.; Russell L. Kreeger, Flemington; George A. Salensky, White House Station, both of N.J.

[73] Assignees: Medical College of Hampton Roads, Arlington, Va.; Biomaterials Corporation, Plainsboro, N.J.

[21] Appl. No.: 418,884

[22] Filed: Apr. 7, 1995

Related U.S. Application Data

[63] Continuation of Ser. No. 129,253, Sep. 29, 1993, abandoned.

[51] Int. Cl.$^6$ .................................................. A61K 31/72
[52] U.S. Cl. ............................ 514/57; 514/59; 514/55; 514/814; 514/843; 514/935; 514/944; 514/945; 536/44; 536/55.1; 536/99; 424/DIG. 14
[58] Field of Search ........................... 514/814, 843, 514/55, 57, 59, 935, 944, 945; 536/99, 44, 55.1; 424/DIG. 14

[56] References Cited

U.S. PATENT DOCUMENTS

| | | | |
|---|---|---|---|
| 4,228,277 | 10/1980 | Landoll | 536/90 |
| 4,242,359 | 12/1980 | Cooper et al. | 424/325 |
| 4,284,003 | 5/1983 | Kazmiroski et al. | 424/341 |
| 4,321,277 | 3/1982 | Saurino | 424/329 |
| 4,387,094 | 6/1983 | Bagros | 424/180 |
| 4,459,289 | 7/1984 | Maltz | 424/180 |
| 4,474,769 | 10/1984 | Smith | 424/180 |
| 4,551,148 | 11/1985 | Riley et al. | 604/890 |
| 4,663,159 | 5/1987 | Brode et al. | 424/70 |
| 4,707,362 | 11/1987 | Nuwayser | 424/433 |
| 4,845,175 | 7/1989 | Lo | 526/200 |
| 4,929,722 | 5/1990 | Partain et al. | 536/20 |
| 4,946,870 | 8/1990 | Partain et al. | 514/777 |

FOREIGN PATENT DOCUMENTS

| | | |
|---|---|---|
| 0189935 | 8/1986 | European Pat. Off. . |
| 2078110 | 1/1982 | United Kingdom . |

OTHER PUBLICATIONS

The Effects of Frequent Nonoxynol–9 Use On The Vaginal and Cervical Mucosa Somchai Niruthisard, MD et al., pp. 176–179, 1991.

Comparison of Vaginal Tolerance Test of Spermicidal Preparations in Rabbits and Monkeys P. Eckstein et al., pp. 85–93, 1969.

HEC Cellosize Hydroxyethyl Cellulose–Union Carbide Corporation, pp. 1–32, 1991.

*Primary Examiner*—Michael G. Wityshyn
*Assistant Examiner*—Francisco C. Prats
*Attorney, Agent, or Firm*—Banner & Witcoff Ltd.

[57] ABSTRACT

Improved contraceptive compositions are disclosed which comprise a spermicide or virucide, a polymeric delivery component and optionally a cosmetic ingredient. The improvement is directed to the use of certain hydrophobically modified polysaccharides as the polymeric delivery component. Quite advantageously, the hydrophobically modified polysaccharides of the present invention can alter sperm motility. Moreover, the hydrophobically modified polysaccharides can provide reduced irritation potential when used in combination with spermicides such as, for example, nonoxynol-9, which may reduce the potential for infection of sexually transmitted diseases such as HIV and herpes.

8 Claims, No Drawings

CONTRACEPTIVE COMPOSITIONS

This invention was made with government support under Cooperative Agreement DPE-3044-A-00-6063-00 between the United States Agency for International Development and the Medical College of Hampton Roads. The government has certain rights in this invention.

This application is a continuation of application Ser. No. 08/129,253, filed Sep. 29, 1993, now abandoned.

FIELD OF THE INVENTION

The present invention generally relates to contraceptive compositions, and more specifically relates to improved contraceptive compositions comprising certain hydrophobically modified polysaccharides as polymeric delivery components.

BACKGROUND OF THE INVENTION

Contraceptive compositions typically comprise an active ingredient, such as, for example, nonoxynol-9, a polymeric delivery component for delivering the active ingredient, such as, for example, hydroxyethyl cellulose or carboxymethyl cellulose, cosmetic ingredients, such as, for example, water, sorbitol and propylene glycol, and optionally other ingredients, such as, for example, stabilizers, fragrances, viscosity adjusters, and the like.

One important attribute of contraceptive compositions is that the active ingredients should be effective as a spermicide. In addition, the other ingredients present in the contraceptive compositions should not interfere with the effectiveness of the active ingredient. Many existing contraceptive compositions possess these properties. However, such existing contraceptive compositions typically do not have a high degree of substantivity to the mucosal lining of the vagina. Moreover, existing polymeric delivery components generally do not provide any functional effect with respect to altering sperm motility.

Spermicides such as nonoxynol-9 and benzalkonium chloride have been used effectively as active ingredients in contraceptive compositions for many years. However, it has been found that such ingredients can be irritating to the mucosal lining of the vagina and cause an increased risk of vaginal irritation. Along with such increased risks of vaginal irritation, there may be increased risks of contracting sexually transmitted diseases of bacterial, fungal or viral origin, such as, for example, HIV and herpes.

Accordingly, improved contraceptive compositions are desired which are substantive and which can provide a low degree of irritation to the mucosal lining of the vagina. In addition, improved contraceptive compositions are desired wherein polymeric delivery components are provided which can alter sperm motility.

SUMMARY OF THE INVENTION

In accordance with the present invention, improved contraceptive compositions comprising a spermicide or virucide, a polymeric delivery component for the spermicide or virucide and cosmetic ingredients are provided wherein the polymeric delivery component comprises a hydrophobically modified polysaccharide. By virtue of the present invention it is now possible to provide contraceptive compositions wherein the polymeric delivery component can enhance effectiveness of the spermicide. As a result, the overall spermicidal effectiveness of the contraceptive compositions can be improved. In addition, the improved contraceptive compositions of the present invention are substantive to the mucosal lining of the vagina and can provide a reduced degree of vaginal irritation which may lower the risk of contracting sexually transmitted diseases.

DETAILED DESCRIPTION OF THE INVENTION

The contraceptive compositions of the present invention are suitable for use in mammals. As used herein, the term "mammals" means any class of higher vertebrates that nourish their young with milk secreted by mammary glands, e.g., humans, rabbits and monkeys.

The spermicides useful in accordance with the present invention are known to those skilled in the art. Typical spermicides include, for example, benzalkonium chloride, octoxynol-9, ricinoleic acid, phenol mercuric acetates and nonoxynol-9, etc. Nonoxynol-9 and benzalkonium chloride are preferred spermicides for use in accordance with the present invention.

The virucides suitable for use in the contraceptive compositions of the present invention are known to those skilled in the art. Typical virucides include, for example, acyclovir, idoxyurnidine, ribavirin, nonoxynol-9, vidarabine and rimantadine.

Thus, the contraceptive compositions of the present invention may typically comprise one or more spermicide or one or more virucide or both. Some ingredients such as, for example, nonoxynol-9, may function both as spermicide and virucide.

The total amount of spermicide and virucide, or mixtures thereof, will typically range from about 0.1 to 50 weight percent based on the weight of the contraceptive composition. Preferably, the amount of spermicide or virucide employed will be that amount necessary to achieve the desired spermicidal or virucidal results. Appropriate amounts can be determined by those skilled in the art. Preferably, the total concentration of the spermicide or virucide, or mixtures thereof, will comprise from about 1 to 25 weight percent, and more preferably from about 1 to 5 weight percent, based on the weight of the contraceptive composition.

The polymeric delivery components suitable for use in the contraceptive compositions of the present invention comprise one or more hydrophobically modified polysaccharides selected from the group consisting of cellulosics and chitosans. Such polysaccharide starting materials from which the hydrophobically modified polysaccharides of the present invention can be made are known to those skilled in the art. Typical cellulosics include, for example, hydroxyethyl cellulose, hydroxypropyl cellulose, methyl cellulose, hydroxypropylmethyl cellulose, hydroxyethyl methyl cellulose, and the like. Preferred cellulosics include hydroxyethyl cellulose and hydroxypropyl cellulose. Typical chitosans include, for example, the following chitosan salts; chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, etc. Chitosan lactate and chitosan pyrrolidone carboxylate and are preferred chitosans. The polymeric delivery component may comprise mixtures of polysaccharides between classes of the group, e.g., cellulosics and chitosans, or within a class, e.g., two cellulosics.

The hydrophobically modified polysaccharides of the present invention comprise a hydrophobic substituent containing a hydrocarbon group having from about 8 to 18 carbon atoms, preferably from about 10 to 18 carbon atoms and more preferably from about 12 to 15 carbon atoms. The hydrocarbon group of the hydrophobic substituent may comprise an alkyl or arylalkyl configuration. As used herein the term "arylalkyl group" means a group containing both aromatic and aliphatic structures. Procedures for hydrophobically modifying the above mentioned polysaccharides are known to those skilled in the art. See, for example, U.S. Pat. Nos. 4,228,277 issued Oct. 14, 1980 and 4,663,159 issued May 5, 1987.

The degree of substitution of the hydrophobic substituent on the polysaccharide is typically from about 0.05 to 0.5, preferably from about 0.08 to 0.25, more preferably 0.08 to 0.16 and most preferably from greater than about 0.11, e.g., 0.12, to less than 0.16, e.g., 0.15, moles of the hydrophobic substituent per mole of polysaccharide. The hydrophobic substituent may be anionic, cationic, nonionic or amphoteric. More than one particular hydrophobic substituent can be substituted onto the polysaccharide provided that the total substitution level is within the ranges set forth above.

A preferred hydrophobic substituent is a cationic, quaternary, nitrogen-containing radical having the formula:

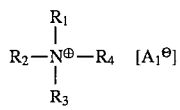

wherein:

each $R_1$ and $R_2$ are $CH_3$ or $C_2H_5$;

$R_3$ is $CH_2CHOHCH_2$ or $CH_2CH_2$;

$R_4$ is an alkyl or arylalkyl group having about 8 to 18 carbon atoms; and $A_1$ is a halide ion.

Preferably, $R_1$ and more preferably, both $R_1$ and $R_2$ are $CH_3$. Preferably, $R_3$ is $CH_2CHOHCH_2$. Preferably, $R_4$ is $C_nH(2n+1)$, where n is from 8 to 18. An especially preferred hydrophobic group, i.e., $R_4$, has the formula $C_{12}H_{25}$. Chlorine is a preferred halide ion.

Other preferred hydrophobic substituents include those prepared from hydrophobe containing reagents such as glycidyl ethers, e.g., nonylphenylglycidyl ether or dodecylphenylglycidyl ether, alphaolefin epoxides, e.g., 1,2 epoxy hexadecane and their respective chlorohydrins, alkyl halides, e.g., dodecylbromide, and mixtures thereof.

The ionic character of the hydrophobically modified polysaccharides of the present invention is not critical and can be anionic, cationic, nonionic or amphoteric. However, cationic polysaccharides are preferred for use in accordance with the present invention. Thus, in a preferred aspect of the invention, the polysaccharides are also substituted with an ionic substituent in addition to the hydrophobic substituent. The amount of ionic substituent typically ranges from about 0.05 to 0.9, preferably from 0.10 to 0.25, moles of the ionic substituent per mole of the polysaccharide for cellulosics and preferably from about 0.5 to 0.9 moles of the ionic substituent per mole of the polysaccharide for chitosan derivatives. More than one particular ionic substituent can be substituted onto the polysaccharide provided that the total substitution level is within the ranges set forth above.

A preferred cationic substituent for cellulosics is a cationic quaternary nitrogen containing radical having the formula:

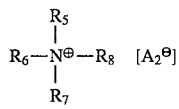

wherein each $R_5$, $R_6$ and $R_7$ are $CH_3$ or $C_2H_5$;

$R_8$ is $CH_2$ $CHOHCH_2$ or $CH_2CH_2$; and $A_2$ is a halide ion.

Preferably, at least one of $R_5$, $R_6$ and $R_7$ are $CH_3$. Preferably $R_8$ is $CH_2CHOHCH_2$. Preferably, $A_2$ is a chloride anion.

A preferred cationic substituent for chitosans is an ammonium group containing radical having the formula:

wherein $A_3$ is an organic acid counter ion. Preferably, $A_3$ is lactate pyrrolidone carboxylate, acetate or combinations thereof.

In addition to the above described hydrophobically modified polysaccharides, the contraceptive compositions may contain other polysaccharides, or derivatives thereof, such as, for example; hydroxyethyl cellulose, carboxymethyl cellulose, dextran sulfate and hyaluronic acid. Such other polysaccharides may or may not be hydrophobically modified. Such other polysaccharides, when present in the composition, may comprise from about 0.1 to 25%, based on the weight of the contraceptive compositions. One preferred contraceptive composition in accordance with the present invention comprises a cationic hydrophobically modified hydroxyethyl cellulose in combination with chitosan lactate as the polymeric delivery component.

Preferably, the hydrophobically modified polysaccharides of the present invention are water soluble. As used herein, the term "water soluble" means that at least 1 gram and preferably at least 2 grams of the hydrophobically modified polysaccharide are soluble in 100 grams of distilled water at 25° C. and 1 atmosphere. The degree of water solubility can be controlled by varying the amount of ether substitution, hydrophobe substitution and cation substitution on the polysaccharide, the details of which are known to those skilled in the art.

The molecular weight of the polysaccharides suitable for use in accordance with the present invention typically ranges from about 10,000 to 500,000 grams per gram mole and preferably ranges from about 20,000 to 200,000 grams per gram mole. As used herein, the term "molecular weight" means weight average molecular weight. Methods for determining weight average molecular weight of polysaccharides are known to those skilled in the art. One preferred method for determining molecular weight is low angle laser light scattering. The viscosity of the polysaccharides typically ranges from about 5 to 5000 centipoise, preferably from about 10 to 500 centipoise. Unless otherwise indicated, as used herein the term "viscosity" refers to the viscosity of a 2.0 weight percent aqueous solution of the polymer measured at 25° C. with a Brookfield viscometer. Such viscosity measuring techniques are known to those skilled in the art.

Typically, the amount of the polymeric delivery component will range from about 0.1 to 99.9 weight percent, preferably, from about 0.5 to 50 weight percent and more preferably from about 1 to 10 weight percent, based on the weight on the contraceptive composition.

The balance of the contraceptive compositions of the present invention, i.e., typically from about 0.1 to 99.8% and often about 50 to 99.8 weight percent, may optionally comprise one or more cosmetic ingredients. Such cosmetic ingredients are known to those skilled in the art and are often referred to in the art as diluents, solvents and adjuvants. Typically cosmetic ingredients include, for example; water, ethyl alcohol, isopropyl alcohol, glycerin, glycerol propylene glycol, sorbitol and other high molecular weight alcohols. In addition, contraceptive compositions of the present invention may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20osorbitan monolaurate is a preferred stablizer for use in the compositions of the present invention. In fact, in accordance with the present invention, it is believed that certain stabilizers, such as, for example, polyoxyethylene 20-sorbitan monolaurate, may contribute to the sperm blocking properties of the hydrophobically modified polysaccharides of the present invention. Details concerning the selection and amounts of cosmetic ingredients, other additives, and blending procedures are known to those skilled in the art.

The contraceptive compositions of the present invention may be delivered to the vagina of a mammal by any means known to those skilled in the art. Typical forms for delivery of the compositions include, for example; creams, lotions, gels, foams, sponges, suppositories and films. In addition the compositions of the present invention may be used as personal care lubricants, such as, for example, as condom lubricants, and the like. Such lubricants may comprise commonly known ingredients such as, for example: humectants; e.g., glycerine, sorbitol, mannitol, glycols and glycol ethers; buffers, e.g., glucono-d-lactone; germicides or bactericides, e.g., chlorhexidine gluconate; preservatives, e.g., methylparaben; viscosifiers; e.g., hydroxyethyl cellulose, etc.; other adjuvents; e.g., colors and fragrances; in addition to the compositions of the present invention. Those skilled in the art will recognize that the physical properties, e.g., viscosity, of such delivery forms may vary widely. For example, the viscosity of a gel form of the composition of the present invention, e.g. 150,000 centipoise, may be substantially higher than the viscosity of lotion form of the composition of the present invention, e.g., 100 centipoise. Further details concerning the materials, ingredients, proportions and procedures of such delivery forms are known to those skilled in the art.

The contraceptive compositions of the present invention are preferably administered to the vagina of the mammal in a dosage which is effective to immobilize sperm present in the vagina and/or to inhibit their penetration in cervical mucus. Typical dosages range between about 0.01 to 0.2 grams of the composition per kilogram of body weight of the mammal.

Quite surprisingly, it has been found that the hydrophobically modified polysaccharides of the present invention can provide a high degree of substantivity to the mucous membrane of the vagina, in addition to being non-irritating to the mucous membrane even in the presence of normally irritating active ingredients such as Nonoxonyl-9. Moreover, the hydrophobically modified polysaccharides of the present invention can provide a high degree of saline compatibility. Saline compatability is an important attribute of contraceptive compositions. As used herein, the term "saline compatability" means that the contraceptive composition remains dissolved, i.e., does not separate at 25° C. and 1 atmosphere, in a saline solution, i.e., 9 grams of NaCl per liter of water, at concentrations of up to at least 2 weight percent, preferably 5 weight percent, for at least one hour, preferably at least 24 hours. Preferably, there are appropriate levels of the hydrophobic substituent and the ionic substituent to enhance the saline compatibility of the composition. The molar ratio of the ionic substituent to the hydrophobic substituent is preferably at least 1.5:1, more preferably 2.0:1 and most preferably at least 2.5:1. When the hydrophobic substituent is not ionic, the molar ratio of the ionic substituent to the hydrophobic substituent is equal to the molar ratio of the ionic substituent to the hydrophobic substituent. When the hydrophobic substituent is ionic, the molar ratio of the ionic substituent to the hydrophobic substituent is equal to the sum of the moles of ionic substituents and hydrophobic substituents per mole of hydrophobic substituent. For example, if the substitution level of a cationic, hydrophobic substituent is 0.12 gram moles per gram mole of polysaccharide, and the substitution level of the cationic substituent is 0.2 gram moles per mole of polysaccharide, then the molar ratio of the ionic substituent to the hydrophobic substituent would be 2.67, i.e., $(0.12+0.20) \div 0.12 = 2.67$.

Thus, the compounds of the present invention are particularly suitable for use as excipients for contraceptive compositions because of their desirable combination of saline compatibility, low irritation potential, substantivity and ability to impair sperm motility.

EXAMPLES

The following examples are provided for illustrative purposes and are not intended to limit the scope of the claims which follow.

DEFINITIONS

The following ingredients were used in the Examples.

CMC—carboxymethyl cellulose having a viscosity of 400–800 centipoise, available from Aqualon Company, Wilmington, Del.

CL—chitosan lactate having a 1% solution viscosity of 15 to 250 centipoise, available from Dainichiseika Colors and Chemicals Co. Ltd., Tokyo, Japan.

CONCEPTROL—a commercially available contraceptive composition containing CMC and POV sold by Advanced Care Products, Ortho, Johnson and Johnson, New Brunswick, N.J.

CS1—2,3 epoxypropyl trimethyl ammonium chloride available from DeGussa Corporation, sold as Quab 151.

DS—dextran sulfate having a molecular weight of 40,000–50,000 g/gmole, available from United States Biomedical Corp., Cleveland, Ohio.

HEC1—hydroxyethyl cellulose having a viscosity of 4400–6000 centipoise (1% solution) available from Union Carbide Corp., Danbury, Conn., sold as Cellosize® QP-100 M.

HPC1—hydroxypropyl cellulose having a viscosity of 1500–3000 centipoise (1% solution) available from Aqualon Company, Wilmington, Del.

HS1—3-chloro-2-hydroxypropyl dimethyldodecyl ammonium chloride available from DeGussa Corporation, Ridgefield Park, N.J., sold as Quab 342.

HS2—3-chloro-2-hydroxypropyl dimethyloctadecyl ammonium chloride available from DeGussa Corporation, Ridgefield Park, N.J., sold as Quab 426.

HS3—nonylphenylglycidyl ether available from Rhone Poulenc sold as Heloxy 64.

JR—a cationic hydroxyethyl cellulose having a viscosity of 300–500 centipoise available from Union Carbide Corp., Danbury, Conn.

N-9—Nonoxynol-9 USP available from Rhone Poulenc, Cranberry, N.J., sold as Igepal CO-630 Special.

P-20—polyoxyethylene 20-sorbitan monolaurate, available from ICI Americas, Inc., Wilmington, Del., sold as Tween 20.

P-80—polyoxyethylene 80-sorbitan mono-oleate, available from ICI Americas, Inc., Wilmington, Del., sold as Tween 80.

PG—propylene glycol USP, available from Fisher Scientific, Fairlawn, N.J.

POL. 1—a cationic, hydrophobically modified hydroxyethyl cellulose having a viscosity of 100 to 500 centipoise (2% solution) and containing a hydrophobic substituent containing a hydrocarbon portion having 12 carbon atoms and a cationic substituent, available from Union Carbide, Danbury, Conn. sold as Quatrisoft®.

POL. 2—a cationic, hydrophobically modified hydroxyethyl cellulose having a viscosity of 50 to 500 (2% solution) centipoise and containing a hydrophobic substituent containing a hydrocarbon portion having 12 carbon atoms and a cationic substituent.

POL. 3—a cationic, hydrophobically modified hydroxyethyl cellulose having a viscosity of 50 to 500 (2% solution) centipoise and containing a hydrophobic substituent containing a hydrocarbon portion having 18 carbon atoms and a cationic substituent.

POL. 4—a non-ionic hydrophobically modified hydroxyethyl cellulose having a molecular weight of 300,000 g/gmole having a hydrophobic substituent containing a hydrocarbon portion having 16 carbon atoms available from the Aqualon Company, Wilmington, Del., sold as Natrosol® Plus.

POL. 5—a hydrophobically modified dextran sulfate having a molecular weight of 50,000 g/gmole and containing 2.8 wt. % of a hydrophobic substituent containing a hydrocarbon portion having 15 carbon atoms.

POL. 6—a hydrophobically modified carboxymethyl cellulose having a viscosity of 50 to 500 (2% solution) centipoise and containing 1.2 wt. % of a hydrophobic substituent containing a hydrocarbon portion having 15 carbon atoms.

POV—polyvinyl pyrrolidone Povidone USP having a molecular weight of 45,000 g/gmole, available from ISP Chemicals Wayne, N.J.

SOR—sorbitol, available from Fisher Scientific, Fairlawn, N.J.

The following tests were used in the Examples.

Modified One End Test (MOET)—This test was used to determine the effect of various compounds on sperm penetration in cervical mucus. Capillary tubes containing bovine cervical mucus obtained from Serono-Baker Diagnostics Inc., Allentown, Pa. sold as Penetrax, were used to conduct the test. Each of the test compositions containing the polymer to be tested was diluted in a saline solution, i.e., at 9 grams of NaCl per liter of water, to a polymer concentration of between 0.007 w/v % and 0.45 w/v % (w/v % equals grams per 100 milliliters). The test was conducted at a concentration of either 0.003 w/v% polymer, 0.007 w/v % polymer or 1 g of test composition per 11 ml of saline. The tubes were thawed briefly and then broken open. The open end was placed in a container containing the sample in saline. The sample was allowed to migrate for 30 minutes through the tube. A semen sample was then diluted with a buffer solution to 60 million motile sperm per milliliter and mixed with the polymer sample. The tube containing the polymer sample was then re-inserted into the container containing the mixed solution and stored in an incubator at 37° C. in an atmosphere of 5 percent carbon dioxide in air for 60 minutes. The container and tube were then removed from the incubator and the tube was visually analyzed under a microscope for the migration of motile vanguard sperm through the tube. The results are expressed as percentage of migration as compared to control samples. In the control samples, the tubes were incubated with saline containing no polymer.

Double End Test (DET)—This test was also used to biologically evaluate the diffusion of the compounds in cervical mucus. The DET is similar to the MOET with the exception that 20 millimeter capillary tubes were exposed to the polymer samples by one end for 60 minutes and subsequently by the other end to the semen solution for 60 minutes so that sperm could migrate in the opposite direction of the polymer sample. Penetration length of vanguard motile sperm is recorded and the results are expressed as percentage of migration as compared to control samples, i.e., saline containing no polymer. The shorter the sperm penetration, the greater the compound biodiffusion. In addition, the samples used for the DET were further modified to contain 4 weight percent of N-9. The DET values reflect how far a test compound can physically diffuse in cervical mucus while still displaying sperm penetration inhibitory activity.

Simultaneous One End Test (SOET)—This test was used to detect the quick blocking effects of the compounds particularly exerted through sperm motility alterations. The SOET is similar to the MOET except that the solution containing the polymer is mixed with the semen sample and then one end of the capillary tube containing bovine cervical mucus is inserted into the mixture of the polymer and semen sample and stored in an incubator at 37° C. in an atmosphere of 5% carbon dioxide in air for 60 minutes. Penetration length of vanguard motile sperm is recorded and the results are expressed as percentage of migration as compared to control samples, i.e., saline containing no polymer. In the SOET, if not impeded by the test compound, the sperm have the ability to migrate into the tube immediately after contact.

Sander-Cramer test—This test was used to evaluate the spermicidal effectiveness of contraceptive compositions. The Sander-Cramer test was developed in the laboratories of Ortho Pharmaceutical Corporation. A slight modification of the original protocol was used as described below. Serial dilutions of each test composition in volumes of 250 microliters were added to 50 microliters of semen adjusted to 60 million motile sperm per milliliter at room temperature. The end point was the greatest. dilution at which all of the sperm were immobilized within 20 seconds. Results are expressed as minimum effective concentrations in milligrams per milliliter.

Example 1

Preparation of Cellulose Ether Derivative

A reaction vessel equipped with a stirrer, condenser, addition funnels, and nitrogen supply, was charged with 39 grams of HEC1 and 272 grams of anhydrous acetone. The reactor was purged with nitrogen and 23 grams of an aqueous sodium hydroxide solution containing 20 wt % sodium hydroxide was added. After stirring for 30 minutes, 64 g of an aqueous solution containing 40 wt % HS1 was added. The reactor mixture was heated to 55° C. and held there for 2 hours. Then 8.7 grams of an aqueous solution containing 70 wt % CS1 was added. The mixture was held at 55° C. for another hour. The reaction was cooled and neutralized with 3 grams glacial acetic acid. The reaction slurry was filtered and washed 7 times with 400 grams of an aqueous solution containing 90 wt % acetone, once with 400 grams of an aqueous solution containing 94 wt % acetone, and once with 400 grams of a solution containing 0.5 milliliter of a 40 wt % glyoxal solution, 0.5 milliliter of acetic acid and the balance acetone. After drying, 58 grams of product containing 1.5% volatiles was obtained. The nitrogen content of the polymer was 1.60 wt. %, and the polymer had a 2% solution viscosity of 190 centipoise.

Example 2

Nonoxynol-9 Compatibility

In order to compare the compatibility of nonoxynol-9 with non-hydrophobically modified polymeric delivery components and the polymeric delivery components of the present invention, the following example was conducted. HEC1, HPC1 and POL.4 were used in this Example.

One hundred gram aqueous solutions containing 1.5 weight percent of the polymeric delivery component being tested were prepared. To each solution, 4.16 grams of N-9 were added and mixed for 20 minutes. Each solution was then divided into two portions. The first portion was stored at room temperature, i.e., about 25° C., and the second solution was stored at about 35° C. After 24 hours, the solution containing HEC1 demonstrated a phase separation which indicated that the HEC1, which was not hydrophobically modified, was incompatible with N-9. Similarly, after 24 hours the solution containing HPC1 also demonstrated a phase separation and thus, was incompatible with N-9. Quite surprisingly, even after 96 hours, the solution containing the POL.4 did not demonstrate a phase operation. Thus, the hydrophobically modified hydroxyethyl cellulose was compatible with the N-9.

Example 3

Preparation of Test compositions and Their Sperm Penetration

Inhibitory Activity (1) Polymer POL. 2 was dissolved in deionized filtered water to form a 2.5 wt. % solution. The polymer solids, as determined in a 100° C. oven for 2 hours, was 95.4 wt. %. Thereafter, 2.62 grams were dissolved in 97.38 grams of water with good agitation and heated to 75° C. for complete solution. The pH of the solution was adjusted to 4.7 with lactic add. The solution viscosity as determined by a Brookfield Cone & Plate Viscometer Model DV-1 CP-41 at 20 rpm was 609 centipoise. The 2.5 wt. % solution was then used to make test compositions with varying polymer solids content by dilution with water.

(2) A test composition containing 1.25 wt. % polymer and 1.25 wt. % P-20 was prepared by mixing 50 grams of the above 2.5 wt. % solution (1) with 1.25 grams of P-20 and 48.75 grams of water. The MOET was then performed using a sample containing 1 g of the test composition per 11 ml saline. The MOET value was 0% indicating an exceptional reduction in sperm penetration in cervical mucus. This finding is particularly important since the same sample failed to completely immobilize sperm under the conditions employed in the Sander-Cramer test. The MOET value was 12% at a polymer concentration of 0.007 w/v% also indicating an exceptional reduction in sperm penetration in cervical mucus.

(3) An additional quantity of the above test composition was used to prepare a 4 wt. % N-9 composition containing 1.25 wt. % polymer and 1.25 wt. % P-20. Approximately 96 grams of the test composition described in (2) above was mixed with 4.0 grams of N-9 for 30 minutes. The DET was then performed and the result showed a sperm penetration of 60%. This reveals a compound cervical mucus biodiffusion similar to N-9 alone, and certainly better than the penetration achieved by CONCEPTROL containing the same amount of N-9. Sander-Cramer spermicidal testing showed the composition to be effective at 0.132 mg of N-9 per milliliter.

Several cellulose ether derivatives were prepared in accordance with the procedure set forth in Examples above. The cellulose ether derivatives were then formulated into compositions suitable for evaluation purposes. The compositions were formulated to contain either 1.25 or 2.5 weight percent of the cellulose ether, 0, 1.25 or 2.5 weight percent of P-20 with the balance comprising water. The levels of the hydrophobic substituent and the ionic substituent, as well as the amount of cellulose ether in the samples are set forth in Table 1 below. In addition, MOET values are also set forth in Table 1.

TABLE 1

CONTRACEPTIVE COMPOSITIONS

| SAMPLE | POLYMER | AMOUNT OF P-20 WT % | AMOUNT OF CELLULOSE ETHER WT % | HYDROPHOBIC SUBSTITUENT TYPE | HYDROPHOBIC SUBSTITUENT AMOUNT mol/mol | IONIC SUBSTITUENT TYPE | IONIC SUBSTITUENT AMOUNT mol/mol | MOET (0.007 W/V %) | MOET 1 g test composition per 11 ml)) |
|---|---|---|---|---|---|---|---|---|---|
| 1 | POL. 1 | 1.25 | 1.25 | HS1 | 0.08 | | | 50 | |
| 2 | POL. 2 | 1.25 | 1.25 | HS1 | 0.12 | CS1 | 0.23 | 12 | 0 |
| 3 | POL. 2 | 1.25 | 1.25 | HS1 | 0.16 | CS1 | 0.08 | 64 | |
| 4 | POL. 3 | 2.5* | 2.5 | HS2 | 0.04 | CS1 | 0.06 | 53** | |
| 5 | POL. 2 | 1.25 | 1.25 | HS1 | 0.06 | CS1 | 0.10 | 7 | |
| 6 | HEC 1 (Control) | 0 | 3.0 | | | | | | 100 |
| 7 | JR (Control) | 0 | 6.0 | | | CS1 | 0.40 | | 89 |

TABLE 1-continued

| | | | | HYDROPHOBIC SUBSTITUENT | | IONIC SUBSTITUENT | | MOET | MOET 1 g test |
|---|---|---|---|---|---|---|---|---|---|
| SAMPLE | POLYMER | AMOUNT OF P-20 WT % | AMOUNT OF CELLULOSE ETHER WT % | TYPE | AMOUNT mol/mol | TYPE | AMOUNT mol/mol | (0.007 W/V %) | composition per 11 ml)) |
| 8 | POL. 4 | 0 | 3.0 | | | | | | 77 |
| 9 | POL. 1/CL*** | 2.5 | 1.25 | HS1 | 0.08 | | | 31 | 0 |
| 10 | CMC/POV (control) | 0 | 2.5 | | | | | 95 | 97 |
| 11 | POL. 5 | 1.25 | 1.25 | HS3 | | | | | 40 |
| 12 | POL. 6 | 1/25 | 1.25 | HS3 | | | | | 22 |

*P-80 substituted for P-20
**tested at polymer concentration of 0.003 w/v %
***0.625 wt. % POL. 1 and 0.625 wt. % CL.

The data in Table 1 demonstrate that, quite surprisingly, the cationic, hydrophobically modified cellulose ethers, i.e., POL. 1, POL. 2 and POL. 3, provided significant sperm blocking properties, i.e., MOET values less than 65% at a polymer concentration of 0.007 w/v %. In addition, POL. 4, which is hydrophobically modified and nonionic provided a MOET value of 77% as compared to unmodified HEC1 which provided a MOET value of 100% at a test composition concentration of 1 g/11 milliliters. A cationic cellulose ether, i.e., JR (Control), which was not hydrophobically modified, provided a MOET of 89% at a test composition concentration of 1 g/11 milliliters. Two hydrophobically modified anionic polysaccharides, i.e., POL. 5 and POL. 6, provided MOET values of 40% and 22% respectively at a test composition concentration of 1 gram per 11 milliliters which demonstrated less preferable blocking capability as compared to the cationic hydrophobically modified polysaccharides, e.g., POL. 2, which had a MOET value of 0% at the same concentration. Thus, the polymeric delivery components of the present invention provided an unpredictable improvement in sperm blocking capability. Preferably, the MOET values for test compositions such as described above which contain the hydrophobically modified polysaccharides of the present invention will be less than 80%, more preferably less than 60%, and most preferably less than 40% when tested in accordance with the MOET procedure outlined above at dilutions of 0.007 w/v %.

Example 4

Sperm Penetration Inhibition

An MOET was run comparing the sperm blocking effect of a hydrophpbically modified polysaccharide, i.e., POL 2, and a saline modifier, i.e., P-20. At a polymer concentration of 0.003 w/v %, the MOET value for POL 2 was 19% and the MOET value for P-20 was 96%. These results clearly demonstrate that the sperm penetration inhibitory activity observed is intrinsic to the hydrophobically modified polysaccharide itself.

Example 5

Sperm Motility and Cervical Mucus Biodiffusion

The Sander-Cramer test was conducted in order to assess the spermicidal effects of the polymer delivery components of the present invention. The DET allowed a biological determination of the compositions diffusion in cervical mucus.

Table 2 below sets forth the results of the Sander-Cramer test and the DET. Several of the above modified samples were compared with a commercially available contraceptive, i.e., CONCEPTROL, to determine if there was any adverse effect of the polymeric delivery components of the present invention on spermicidal activity.

TABLE 2

| | SPERMICIDAL PROPERTIES | | |
|---|---|---|---|
| SAMPLE | N-9 WT % | SANDER-CRAMER MG/ML | DET |
| 1 | 4.0 | 0.201 | 71 |
| 2 | 4.0 | 0.132 | 60 |
| 3 | 4.0 | 0.265 | 61 |
| 4 | 4.0 | 0.163 | 75 |
| 5 | 4.0 | 0.113 | 71 |
| 9 | 4.0 | 0.163 | 74 |
| 10 (control) | 4.0 | 0.113 | 84 |
| CONCEPTROL | 4.0 | 0.114 | 89 |

None of the samples tested demonstrated an adverse effect on the spermicidal activity of the compositions, as shown by the Sander-Cramer Test. According to the DET results, the hydrophobically modified polysaccharides of the present invention facilitated the diffusion of N-9 in cervical mucus without adversely affecting spermicidal properties. This property is very important since the greater the diffusion, the higher the spermicide concentration in the cervical mucus, through which the sperm have to pass in order to reach the mammalian ova. All of the samples which comprised the hydrophobically modified polysaccharides of the present invention, i.e., Samples 1 to 5 and 9, quite unexpectedly, demonstrated significant reductions in the DET values as compared to non-hydrophobically modified polysaccharides, e.g. CONCEPTROL. Thus in addition to providing enhanced sperm blocking properties, the compositions of the present invention also facilitate the diffusion of N-9 in cervical mucus without negatively affecting its spermicidal activity.

Example 6

Correlation Between Sperm Motion Parameters and Cervical Mucus Penetration

Various test compositions were evaluated for SOET values in accordance with the procedure described above. A saline solution provided a value of 100%. A test composition containing POL. 4 provided an SOET of 99%. A test composition containing 50 wt. % POL. 6 and 50 wt. % POV, provided an SOET of 100. In contrast, a test composition containing 50 wt. % POL. 1, i.e., a cationic hydrophobically modified polysaccharide and 50 wt. % CL, provided a SOET of 48%. Similarly, a test composition containing POL. 2, i.e., a cationic hydrophobically modified polysaccharide, provided an SOET of 4.5%. Thus, from this example, it can be seen that, quite surprisingly, the cationic hydrophobically modified polysaccharides of the present invention provide strong and quick inhibition of sperm penetration in cervical mucus.

A computer assisted sperm motion analysis (CASA) was conducted on sperm samples co-incubated several of the polymer samples described above. The details concerning techniques and apparatus relating to CASA are known to those skilled in the art. The apparatus used for this test was obtained from Cryo Resourses Ltd., New York, N.Y., sold under the Cellsoft tradename. The CASA provides an objective description of sperm motion parameters, such as, percent motility, velocity, linearity, amplitude of lateral head displacement, flagellar beat/cross frequency, etc.

Table 3 below sets forth the results of the SOET and CASA testing.

extensively used for testing contraceptive compositions.

A 10-day rabbit vaginal irritation study was conducted at Pharmaco. LSR, an FDA approved testing facility in East Millstone, New Jersey. All aspects of the study were performed in compliance with FDA Good Laboratory Practice and USDA Animal Welfare Regulations.

A total of 45 animals were utilized in this study which was configured as a double blind study. Applications of the appropriate samples in dosages of 1 gram were made once per day for 10 consecutive days. Visual irritation scores were noted each day just prior to dosing and 1 hour post dosing. Following necropsy on day 11, microscopic histopathology examinations were performed at the end of the study. Forty animals had no visual sign of irritation and 5 had responses that were barely perceptible. In order to conduct the post-mortem histopathology, interior, middle and posterior sections of the excised vaginal tissues were examined microscopically. Irritation scores were assigned for the epithelium, leucocytes, congestion, and edema. The scoring system was as follows: minimal irritation 1 to 4; mild irritation 5 to 8; moderate irritation 9 to 11; marked irritation 12 to 16. The scoring system correlated to human irritation potential as follows: scores of 0 to 8 are acceptable, scores of 9 to 11 indicate borderline irritation potential and scores greater than 12 are potentially irritating.

TABLE 3

| Parameters Studied | Semen Samples (Original) | Saline | POL 4 | POL 6/POV | POL 1/CL | POL 2 |
| --- | --- | --- | --- | --- | --- | --- |
| Sperm Motion | | | | | | |
| Concentration | 174.9 | 82.7 | 74.3 | 84.2 | 60.6 | 54.8 |
| Motility (%) | 81.6 | 58.9 | 52.7 | 63.6 | 25.8 | 19.6 |
| Concentration Motile | 142.9 | 51.7 | 48.7 | 56.0 | 15.7 | 10.5 |
| Velocity (um/sec) | 53.8 | 67.7 | 67.1 | 64.2 | 43.2 | 43.5 |
| Linearity | 4.7 | 5.7 | 6.4 | 6.0 | 2.4 | 2.3 |
| ALH mean (um) | 3.3 | 3.1 | 2.4 | 2.9 | 3.2 | 3.0 |
| B/C Frequency (Hz) | 14.5 | 16.6 | 16.3 | 15.8 | 13.2 | 15.7 |
| Cervical Mucus Penetration | | | | | | |
| SOET | | 100 | 99.7 | 100 | 48.2 | 4.5 |

Materials were tested at 0.125% in 0.9% NaCl
ALH: amplitude of lateral head displacement
B/C: flagellar beat/cross
CMP: cervical mucus penetration It can be seen from the data presented in Table 3 that the analysis of sperm motion parameters reveal that quite surprisingly sperm samples incubated with POL 2 and POL 1/CL demonstrated a good correlation between cervical mucus penetration impairment, i.e. SOET values, and sperm motion alteration.

Example 7

Vaginal Tolerance

A correlation exists between rabbits and humans with respect to the irritation potential of vaginal contraceptive compositions. This correlation is well known and used extensively in the pharmaceutical industry. One of the first discoveries of the correlation is reported by P. Eckstein et al. "Comparison of Vaginal Tolerance Tests of Spermicidal Preparations in Rabbits and Monkeys" Journal of Reprod. Fertil., Volume 20, Pages 85 to 93, 1969. It has been found that the rabbit vagina is slightly more sensitive to irritation than the human female vagina. Thus, rabbits have been The histopathology scores are set forth in Table 4 below:

TABLE 4

| VAGINAL TOLERANCE IN RABBITS | | |
| --- | --- | --- |
| SAMPLE | N-9 WT. % | SCORE HISTOPATHOLOGY |
| CONCEPTROL | 4.0 | 4 |
| POL. 1/CL* | 4.0 | 1 |
| POL. 2 | 4.0 | 1 |
| POL. 1/CL* | 2.0 | 1 |
| CONCEPTROL** | 2.0 | 1 |

*1.25 wt. %, POL. 1 and 1.25 wt. % CL
**Formulation similar to CONCEPTROL with 2% N-9.

All of the contraceptive compositions tested provided acceptable histopathology scores as set forth in Table 4. However, quite surprisingly, it was observed that the irritation potential of the contraceptive compositions containing the hydrophobically modified polysaccharides of the present invention, i.e., POL./CL and POL. 2, provided significantly lower histopathology scores for N-9 concentrations of 4.0 weight percent as compared to CONCEPTROL, i.e., 1 versus 4.

Accordingly, the contraceptive compositions of the present invention can provide a low degree of vaginal irritation. This may lead to reduced risks of contracting sexually transmitted diseases such as, for example, HIV and herpes. Moreover, the combination of the hydrophobically modified polysaccharides of the present invention with spermicides such as N-9 can provide synergistic benefits in terms of substantivity, saline compatibility and reduced irritation potential as compared to combinations of unmodified polysaccharides with spermicides.

Example 8

Preparation of Delivery Systems

A contraceptive sponge, a contraceptive film, a contraceptive gel and a contraceptive lotion were prepared as described below.

Contraceptive Sponge

A commercial contraceptive sponge product was purged of N-9 by five washes of isopropyl alcohol and vacuum dried to yield a suitable sponge for impregnating with a POL. 2 contraceptive lotion. The dried sponge weighed 4 g. The sponge was impregnated with 5 grams of a solution containing 1.25 wt. % POL. 2, 1.25 wt. % P-20, and 20 wt. % N-9 to provide 1 gram of spermicide impregnated on the sponge.

The above sponge was characterized by wetting with water, in this case 10 g. It was allowed to equilibrate and then gently squeezed to liberate about 1 gram of fluid. The extract was diluted with water 10 fold and analyzed for nitrogen which showed that POL. 2 was released from the sponge together with the N-9 which was detected by ultraviolet spectroscopy.

Contraceptive Film

Typical commercially available films contain 28 wt. % N-9 and are based on polyvinyl alcohol/glycerine systems. A similar film was prepared by mixing 40 g of a 6 wt. % solution of POL. 2 with 57.4 g of water, 1.2 g. of P-20 and 1.4 g of N-9. This solution was cast on a fluorocarbon release film and placed in a 40° C. oven to produce a 4 mil dry film having a composition of 28 wt % of N-9, 48 wt % POL. 2 and 24 wt. % P-20. The new film had similar physical properties to the commercial contraceptive control film.

Contraceptive Gel

A contraceptive gel was prepared by mixing 2.5 g of a 2.5 wt % aqueous solution of POL. 2 with 2.5 g of 3 wt % solution of POL. 3 and 0.2 g of N-9. A gel was obtained which showed no phase separation after 2 weeks storage.

Contraceptive Lotion

A contraceptive lotion was prepared by combining 62.5 grams of an aqueous solution containing 10 wt. % CL, 104.2 grams of an aqueous solution containing 6 wt. % POL. 1, 25.0 grams of P-20 and 808.3 grams of water. The resulting lotion contained 0.625 et. % POL. 1, 0.625 wt. % CL, 2.5 wt. % P-20 with the balance being water. The contraceptive lotion was completed by adding 4 grams of N-9 to 96 grams of the above mixture.

Those skilled in the art will recognize that although the present invention has been described with respect to specific aspects, other aspects are intended to be included within the scope of the claims which follow. For example, polysaccharides other than those specifically described herein can be used either in place of the polysaccharides described herein. In addition, the compositions of the present invention may be used for antiviral purposes, instead of for contraceptive purposes, e.g., personal care lubricants, to inhibit the transmission of sexually transmitted diseases.

We claim:

1. In a contraceptive composition for use in mammals comprising:
    (a) from about 0.1 to 50.0 wt % of a spermicide selected from the group consisting of benzylalkonium chloride, octoxynol-9, ricinoleic acid, phenol mercuric acetates and nonoxynol-9; a virucide selected from the group consisting of acyclovir, idoxyumidine, ribavirin, nonoxynol-9, vidarabine and rimantadine; or mixtures thereof;
    (b) from about 0.1 to 99.9 wt % of a polymeric delivery vehicle component comprising a cellulosic selected from the group consisting of hydroxyethyl cellulose, hydroxypropyl cellulose, methyl cellulose, hydroxypropylmethyl cellulose and hydroxyethyl methyl cellulose, and mixtures thereof; and
    (c) from about 0.1 to 99.8 wt % of a cosmetic ingredient selected from the group consisting of water, ethyl alcohol, isopropyl alcohol, glycerin, glycerol, propylene glycol, and sorbitol;

the improvement wherein said cellulosic:
    (i) has a molecular weight of from about 10,000 to 500,000 grams per gram mole;
    (ii) is water-soluble; and
    (iii) contains a hydrophobic substituent which is a cationic, quaternary, nitrogen-containing radical having the formula:

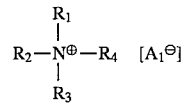

wherein
    each $R_1$ and $R_2$ are $CH_3$ or $C_2H_5$;
    $R_3$ is $CH_2CHOHCH_2$ or $CH_2CH_2$;
    $R_4$ is an alkyl or arylalkyl group having about 8 to 18 carbon atoms; and
    $A_1$ is a halide ion;
        said hydrophobic substituent being present in an amount of from about 0.005 to 0.50 moles of the hydrophobic substituent per mole of the cellulosic and said hydrophobic substituent is present in an amount effective to provide a MOET value of less than 65 % at a polymer concentration of 0.007 w/v %.

2. The composition of claim 1 wherein the alkyl or arylalkyl group comprises from about 10 to 18 carbon atoms.

3. The composition of claim 1 wherein the composition further comprises chitosan lactate.

4. The composition of claim 1 wherein the cellulosic is further substituted with another substituent containing an ionic group in an amount of from about 0.05 to 0.90 moles of the other substituent per mole of polysaccharide.

5. The composition of claim 4 wherein the other substituent is an ammonium group containing radical having the formula:

wherein $A_3$ is an organic acid counter ion.

6. The composition of claim 1 which further comprises polyoxyethylene 20-sorbitan monolaurate, polyoxyethylene 80-sorbitan mono-oleate, or mixtures thereof.

7. The composition of claim 1 in the form of a cream, lotion, gel, foam, sponge, suppository or film.

8. A personal care lubricant composition comprising the composition of claim 1 and at least one of a humectant, a viscosifier, a buffer, a germicide and a bactericide.

* * * * *